United States Patent [19]

Berninger

[11] Patent Number: 5,229,283
[45] Date of Patent: * Jul. 20, 1993

[54] USE OF EXO-SAMPLE NUCLEOTIDES IN GENE CLONING

[75] Inventor: Mark S. Berninger, Gaithersburg, Md.

[73] Assignee: Life Technologies, Inc., Gaithersburg, Md.

[*] Notice: The portion of the term of this patent subsequent to Aug. 11, 2009 has been disclaimed.

[21] Appl. No.: 880,009

[22] Filed: May 8, 1992

Related U.S. Application Data

[63] Continuation of Ser. No. 715,623, Jun. 14, 1991, Pat. No. 5,137,814.

[51] Int. Cl.⁵ ............... C12N 15/00; C12N 15/10; C12P 19/34; C12Q 1/68
[52] U.S. Cl. .................. 435/172.3; 435/6; 435/91
[58] Field of Search ................. 435/91, 6, 172.3

[56] References Cited

U.S. PATENT DOCUMENTS 4,873,192  10/1989  Kunkel ................. 435/172.3
5,035,996   7/1991  Hartley ................. 435/6
5,137,814   8/1992  Rashtchian et al. ........ 435/91

FOREIGN PATENT DOCUMENTS 329822  8/1989  European Pat. Off. .

OTHER PUBLICATIONS

Longo, M. C. et al., *Gene* 93:125–128 (1990).
Frohman, M. A. et al., *Proc. Natl. Acad. Sci. (U.S.A.)* 85:8998–9002 (1988).
Ohara, O. et al., *Proc. Natl. Acad. Sci. (U.S.A.)* 86:5673–5677 (1989).
Duncan, B., *The Enzymes* XIV:565–586 (1981).

Primary Examiner—Richard A. Schwartz
Assistant Examiner—Philip W. Carter
Attorney, Agent, or Firm—Jeffrey I. Auerbach

[57] ABSTRACT

The present invention provides improved methods for manipulating recombinant DNA in gene cloning and expression. More specifically, the invention provides methods capable of altering a nucleic acid sequence present at the termini of a target sequence.

14 Claims, 9 Drawing Sheets

યુ.એસ. Pat. No. 5,137,814.

USE OF EXO-SAMPLE NUCLEOTIDES IN GENE CLONING

This application is a continuation of U.S. patent application Ser. No. 07/715,623 (filed Jun. 14, 1991) now U.S. Pat. No. 5,137,814.

FIELD OF THE INVENTION

The invention relates to improved methods for manipulating recombinant DNA in gene cloning and expression. More specifically, the invention provides a method in which exo-sample nucleotides are used to alter either the 3' or 5' terminus of the nucleic acid sequence of a target sequence.

BACKGROUND OF THE INVENTION

Recombinant DNA methodologies capable of amplifying purified nucleic acid fragments have long been recognized. Typically, such methodologies involve the introduction of a desired nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning: A Laboratory Manual*, Cold Spring Harbor Laboratory, 1982, etc.

In some instances, the desired nucleic acid molecule can be readily obtained from a source material. The molecule can then be inserted into a suitable vector by either adding "linker molecules" (see Scheller et al., *Science* 196:177–180 (1977)) or by treating the desired molecule with a restriction endonuclease.

In other instances, however, the desired nucleic acid molecule cannot be obtained from a source material at a concentration or in an amount sufficient to permit gene cloning. In such a situation, it is necessary to amplify the nucleic acid molecule by, for example, template-directed extension, prior to introducing it into a suitable vector. Primer extension can be mediated by the "polymerase chain reaction" ("PCR"), or other means.

Figure 1:
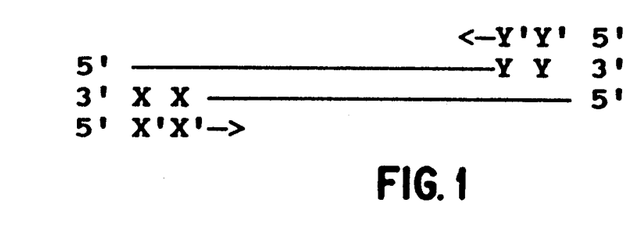
FIG. 1 describes the use of two oligonucleotides complementary to regions of the sequence to be amplified in a PCR amplification process.

In the "polymerase chain reaction" or "PCR" the amplification of a specific nucleic acid sequence is achieved using two oligonucleotide primers complementary to regions of the sequence to be amplified (FIG. 1).

The polymerase chain reaction provides a method for selectively increasing the concentration of a nucleic acid molecule having a particular sequence even when that molecule has not been previously purified and is present only in a single copy in a particular sample. The method can be used to amplify either single or double stranded DNA. Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); Mullis, K. B., et al. (*Met. Enzymol.* 155:335–350 (1987); Erlich H. et al., (EP 50,424; EP 84,796; EP 258,017; EP 237,362); Mullis, K. (EP 201,184); Mullis K. et al., (U.S. Pat. No. 4,683,202); Erlich, H. (U.S. Pat. No. 4,582,788); and Saiki, R. et al. (U.S. Pat. No. 4,683,194) all of which references are incorporated herein by reference).

The ability to incorporate a gene sequence into a suitable vector is typically performed using restriction endonucleases. Thus, the vector and the desired gene sequence are treated with a restriction nuclease capable of producing compatible termini which can then be ligated together to form a covalently closed vector molecule. Preferably, the restriction enzyme is selected such that its recognition site is not present in the desired gene sequence.

It would be desirable to be able to generally alter the nucleotide sequences of a desired target sequence in order to permit it to be cloned into a suitable vector without using oligonucleotide linkers/adapters, and regardless of the availability or suitability of restriction sites. The present invention provides methods suitable for accomplishing these goals.

SUMMARY OF THE INVENTION

The present invention provides improved methods for manipulating recombinant DNA in gene cloning and expression. More specifically, the invention provides methods capable of altering a nucleic acid sequence present at the termini of a target sequence.

In detail, the invention provides a method for incorporating a double-stranded linear desired nucleic acid molecule into a double-stranded vector, comprising:

(A) forming a modified desired nucleic acid molecule characterized in possessing a first region of pre-selected sequence at at least one terminus of a first strand, the sequence containing at least one dU residue;

(B) treating the first region of pre-selected sequence under conditions sufficient to result in the removal of the uracil base of at least one of the dU residues, to thereby form a protruding terminus capable of hydrogen bonding to a complementary sequence on at least one strand of the modified desired molecule;

(C) incubating the modified molecule (B) in the presence of a modified vector having at least one protruding single-stranded terminus, and being capable of hydrogen bonding to at least one of the protruding termini of the modified desired DNA molecule, to thereby incorporate the double-stranded linear desired nucleic acid molecule into the double-stranded vector.

The invention also provides the embodiment of the above method wherein only one terminus of the modified desired molecule contains the dU-containing sequence.

The invention also provides the embodiments of the above methods wherein the terminus is a 3' terminus, or a 5' terminus of the modified desired molecule.

The invention also provides the embodiments of the above methods wherein two termini of the modified desired molecule contain the dU-containing sequence. The invention also provides the embodiments of the above method wherein both of the termini are 3' termini or both of the termini are 5' termini of the modified desired molecule.

The invention also provides the embodiments of the above methods wherein the termini of the first and second strands of the desired DNA molecule contain a plurality of dU residues.

The invention also provides the embodiments of the above methods wherein in step (B), the dU residues are treated with UDG under conditions sufficient to remove the uracil base of at least one of the dU residues, to thereby form an abasic site, or wherein in step (B) additionally comprises treating the abasic site with Endonuclease IV under conditions sufficient to cleave the modified desired molecule at the abasic site.

The invention also provides the embodiments of the above methods wherein the regions of pre-selected sequence of the modified desired DNA molecule are identical.

The invention also provides the embodiments of the above methods wherein in step (C), the two protruding single-stranded termini are produced through the action of a restriction endonuclease, or through the ligation of an oligonucleotide to the vector or by (I) adding to the vector:
  (i) a first region of pre-selected sequence at a 5' terminus of a first strand, the sequence containing at least one dU residue;
  (ii) a second region of pre-selected sequence at a 5' terminus of a second strand, the sequence containing at least one dU residue; and
(II) treating the first and second regions of pre-selected sequence under conditions sufficient to result in the removal of the uracil base of at least one of the dU residues, to thereby form the modified vector having the protruding 3' termini.

The invention further provides a circular nucleic acid molecule comprising:

(A) a double-stranded linear or linearized vector molecule having two termini, A and B, each having a region of pre-selected sequence, and
(B) a double-stranded desired nucleic acid molecule having two termini, I and II, each having a region of pre-selected sequence, wherein the region of pre-selected sequence of a first strand of the vector molecule at termini A and the region of pre-selected sequence of a second strand of the desired nucleic acid molecule at termini I are hybridized to one another; and wherein the region of pre-selected sequence of a second strand of the vector molecule at termini B and the region of pre-selected sequence of a first strand of the desired nucleic acid molecule at termini II are hybridized to one another.

The invention further provides a kit specially adapted to contain in close compartmentalization a first container containing a double-stranded oligonucleotide, having at least one dU nucleotide at a terminus of one strand, and a second container containing an enzyme capable of removing a uracil base of the dU residue.

The invention also provides the embodiments of the above kit which additionally contains a third container containing a linearized double-stranded vector having at least one protruding terminus, the terminus having a sequence which is substantially similar to the nucleotide sequence of the dU-containing strand of the oligonucleotide.

The invention also provides the embodiments of the above kit wherein the terminus is a 3' or a 5' terminus, or wherein two termini of the modified desired molecule contain the dU-containing sequence.

BRIEF DESCRIPTION OF THE FIGURES

FIG. 2 (parts A-C) describes an embodiment wherein the exo-sample nucleotide is incorporated into one strand of a double-stranded oligonucleotide. The target molecule is depicted in FIG. 2A.

FIG. 13 (parts A-C) shows the use of the disclosed method to form a circular vector molecule. In FIGS. 13A and 13B the upper depiction illustrates the structure of the modified desired molecule, and the lower depiction illustrates the structure of the modified vector molecule.

DESCRIPTION OF THE PREFERRED EMBODIMENTS

I. TERMS USED IN MOLECULAR BIOLOGY

In the description that follows, a number of terms used in molecular biology and nucleic acid amplification technology are extensively utilized. In order to provide a clearer and consistent understanding of the specification and claims, including the scope to be given such terms, the following definitions are provided.

"Amplification", as used herein, refers to any in vitro process for increasing the number of copies of a nucleotide sequence or sequences. Nucleic acid amplification results in the incorporation of nucleotides into DNA or RNA. PCR is an example of a suitable method for DNA amplification. As used herein, one amplification reaction may consist of many rounds of DNA replication. For example, one PCR reaction may consist of 10-50 "cycles" of denaturation and replication.

"Nucleotide" as used herein, is a term of art that refers to a base-sugar-phosphate combination. Nucleotides are the monomeric units of nucleic acid polymers, i.e. of DNA and RNA. The term includes ribonucleoside triphosphates, such as rATP, rCTP, rGTP, or rUTP, and deoxyribonucleoside triphosphates, such as dATP, dCTP, dGTP, or dTTP. A "nucleoside" is a base-sugar combination, i.e. a nucleotide lacking phosphate.

"Exo-sample nucleotide", as used herein, refers to a nucleotide which is generally not found in a sequence of DNA. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g. processes involving the enzyme uracil DNA glycosylase (UDG) (Kunkel, U.S. Pat. No. 4,873,192; Duncan, B. K., *The Enzymes XIV*:565–586 (1981), both references herein incorporated by reference in their entirety). Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. Examples of other exo-sample nucleotides include bromodeoxyuridine, 7-methylguanine, 5,6-dihyro-5,6 dihydroxydeoxythymidine, 3-methyldeoxadenosine, etc. (see, Duncan, B.K., *The Enzymes XIV*:565–586 (1981)). Other exo-sample nucleotides will be evident to those in the art. For example, RNA primers used for DNA amplifications can be readily destroyed by alkali or an appropriate ribonuclease (RNase). RNase H degrades RNA of RNA:DNA hybrids and numerous single-stranded RNases are known which are useful to digest single-stranded RNA after a denaturation step.

The presence of deoxyuridine, or any other exo-sample nucleotide, may be readily determined using methods well known to the art. A nucleic acid molecule containing any such exo-sample nucleotide is functionally equivalent to DNA containing only dA, dC, dG or dT (dT is referred to herein as T) in all respects, except that it is uniquely susceptible to certain treatments, such as glycosylase digestion. Numerous DNA glycosylases are known to the art. An exo-sample nucleotide which may be chemically or enzymatically incorporated into an oligonucleotide and a DNA glycosylase that acts on it may be used in this invention. DNA containing bromodeoxyuridine as the exo-sample nucleotide may be degraded by exposure to light under well-known conditions.

The use of exo-sample nucleotides to remove potential contaminants from samples being subjected to PCR amplification is disclosed by Longo, M.C. et al. (*Gene* 93:125–128 (1990), Hartley, U.S. Pat. No. 5,035,966), herein incorporated by reference in their entirety. This reference discloses the use of either dU-containing oligonucleotides or dUTP in the PCR-directed amplification of a target sequence.

The "desired" or "target" gene sequence or nucleic acid molecule is the term used to designate the sequence which is to be either amplified, or incorporated into a vector (which may be circular or linear), in order to achieve the objectives of the present invention. The sequence may be of any size or complexity. In general, some information is known about the desired sequence, such that the sequences of its termini can be ascertained. Any molecule which can be amplified by PCR, or which has restriction sites at its termini can be used as the desired or target sequences of the present invention. A "chimeric molecule is a vector (plasmid, cosmid, viral nucleic acid, etc.) which has been modified to carry or contain the desired gene sequence.

Two sequences are said to be "substantially similar in sequence" if they are both able to hybridize to the same oligonucleotide.

The "terminus" of a nucleic acid molecule denotes a region at the end of the molecule. The term is not used herein as representing the final nucleotide of a linear molecule, but rather a general region which is at or near an end of a linear or circular molecule.

Two termini of two nucleic acid molecules are said to be the "same denominated termini," if the both termini are either the 3' termini of the respective molecules or both termini are the respective 5' termini of the respective molecules. As used herein, the term "same denominated termini," is not intended to refer to the nucleotide sequence of the termini being compared.

As used herein, a DNA molecule is said to be "circular" if it is capable of depiction as either a covalently closed circle, or as a hydrogen bonded circle. A circular molecule may thus be composed of one or more polynucleotides bonded to one another via covalent or hydrogen bonds. The terminal nucleotide(s) of each polynucleotide may either be single-stranded, or may be bonded to another polynucleotide via covalent or hydrogen bonds.

"Uracil DNA glycosylase" (UDG), a term of art, refers to an activity which cleaves the glycosidic bond between the base uracil and the sugar deoxyribose, only when the monomeric nucleotide dUTP is incorporated into a DNA molecule, resulting in incorporation of a deoxyuridine moiety (Duncan, B. in *The Enzymes* 14:565 (1981), ed.: Boyer P). An enzyme possessing this activity does not act upon free dUTP, free deoxyuridine, or RNA (Duncan, supra). The action of UDG results in the production of an "abasic" site. The enzyme does not, however, cleave the phophodiester backbone of the nucleic acid molecule. Most preferably, the phophodiester backbone at an abasic site may be claeved through the use of an endonuclease specific for such substrates. A preferred enzyme for this purpose is the *E. coli* enzyme, Endonuclease IV. Most preferably, Endonuclease IV is used in conjunction with UDG to remove dU residues from a nucleic acid molecule.

"Incorporating" as used herein, means becoming part of a nucleic acid polymer.

"Terminating" as used herein, means causing a treatment to stop. The term includes means for both permanent and conditional stoppages. For example, if the treatment is enzymatic, a permanent stoppage would be heat denaturation; a conditional stoppage would be, for example, use of a temperature outside the enzyme's active range. Both types of termination are intended to fall within the scope of this term.

"Oligonucleotide" as used herein refers collectively and interchangeably to two terms of art, "oligonucleotide" and "polynucleotide". Note that although oligonucleotide and polynucleotide are distinct terms of art, there is no exact dividing line between them and they are used interchangeably herein. An oligonucleotide is said to be either an adapter, adapter/linker or installation oligonucleotide (the terms are synonymous) if it is capable of installing a desired sequence onto a predetermined oligonucleotide. An oligonucleotide may serve as a primer unless it is "blocked.". An oligonucleotide is said to be "blocked," if its 3' terminus is incapable of serving as a primer.

"Oligonucleotide-dependent amplification" as used herein refers to amplification using an oligonucleotide or polynucleotide to amplify a nucleic acid sequence.

An oligonucleotide-dependent amplification is any amplification that requires the presence of one or more oligonucleotides or polynucleotides that are two or more mononucleotide subunits in length and that end up as part of the newlyformed, amplified nucleic acid molecule.

"Primer" as used herein refers to a single-stranded oligonucleotide or a single-stranded polynucleotide that is extended by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis. A primer is typically 11 bases or longer; most preferably, a primer is 17 bases or longer. A minimum of 3 bases may, however, suffice.

"Reaction volume" denotes a liquid suitable for conducting a desired reaction (such as amplification, hybridization, cDNA synthesis, etc.).

A "ligase" is an enzyme that is capable of joining the 3' hydroxyl terminus of one nucleic acid molecule to a 5' phosphate terminus of a second nucleic acid molecule to form a single molecule. Ligase enzymes are discussed in Watson, J. D., *In: Molecular Biology of the Gene,* 3rd Ed., W. A. Benjamin, Inc., Menlo Park, CA (1977), and similar texts.

When an enzymatic reaction, such as a ligation or a polymerization reaction, is being conducted, it is preferable to provide the components required for such reaction in "excess" in the reaction vessel. "Excess" in reference to components of the amplification reaction refers to an amount of each component such that the ability to achieve the desired amplification is not limited by the concentration of that component. When linker/adapter molecules are used after ligation, the excess linker/adapter present in the reaction is preferably separated from the reaction products, or removed from the reaction mix, so that they will not compete with the cloning of the desired sequence. Use of linker/adapter oligonucleotides containing dU residues allows one to destroy excess linker/adapter molecules by enzymatic degradation or other means.

The methods of the present invention are explained partly through illustration. In these illustrations, sequence pairs, such as A and A', B and B', C and C', X and X', and Y and Y', respectively, etc., are complementary to each other. Complementation need not be exact; homology sufficient for proper functioning, e.g. annealing and priming, will suffice.

II. THE METHODS AND MOLECULES OF THE PRESENT INVENTION

The present invention employs exo-sample nucleotides, most preferably the nucleotide dUTP (which, when incorporated into a nucleotide sequence is designated as dU) to create a 3' or 5' overhanging extension in the target nucleic acid molecules. The nucleic acid molecules can be derived from PCR, or other methods, or can be isolated directly from suitable source materials.

A. MODIFICATION OF EITHER THE 3' OR 5' TERMINI OF A DESIRED NUCLEIC ACID MOLECULE USING LINKER/ADAPTER MOLECULES

Figure 2A:
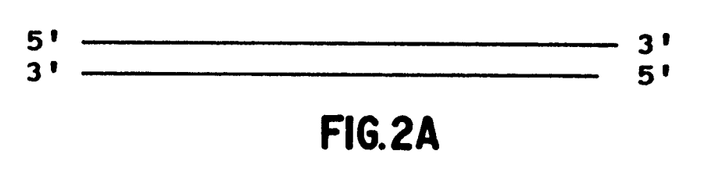
Figure 2B:
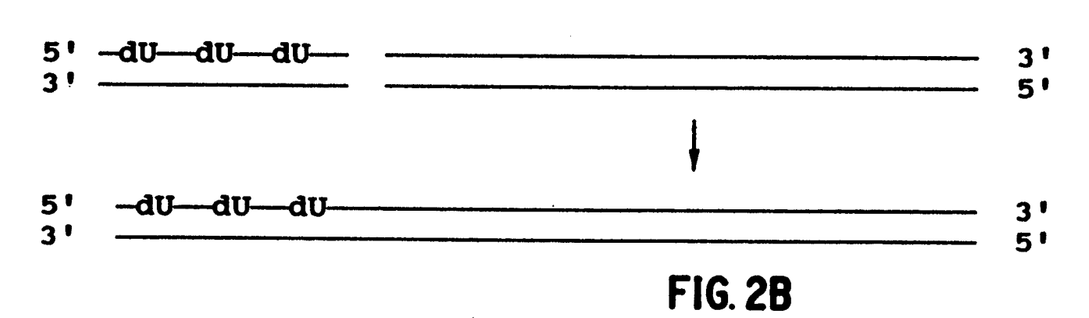
FIG. 2B illustrates the modification of the desired molecule so as to result in the alteration of the terminus of the molecule.
Figure 2C:
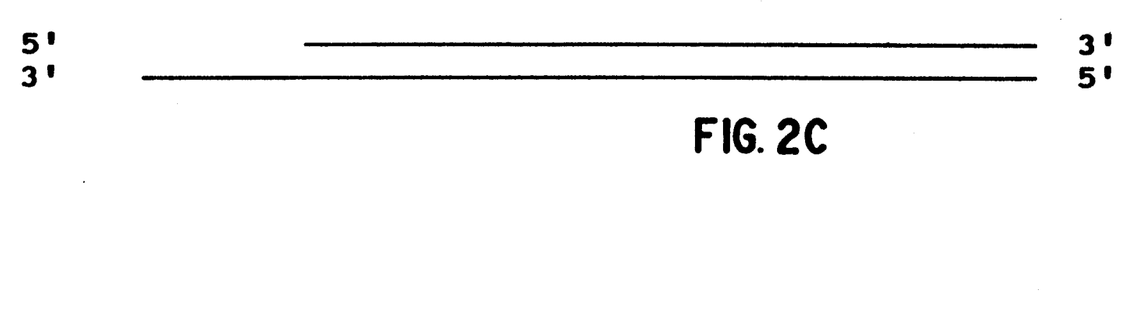
FIG. 2C shows the production of a protruding 3' terminus.

The present invention permits one to modify either the 3' or 5' termini of a desired nucleic acid molecule so as to create either a 5' or 3' single-stranded overhanging region. The invention accomplishes this goal through the use of exo-sample nucleotides, preferably dU. In a first embodiment, the exo-sample nucleotide is incorporated into one strand of a double-stranded oligonucleotide. This oligonucleotide is then ligated to a terminus or to both termini of the desired molecule. Thus, if the target molecule is depicted as shown in FIG. 2A, then to modify the desired molecule so as to produce a protruding 3' terminus, an exo-sample nucleotide is ligated to that terminus (FIG. 2B). Treatment with UDG results in the removal of the uracil base of the dU residues, thereby producing abasic sites. The abasic sites can be cleaved with Endonuclease IV, or similar enzymatic activities, to produce the desired modified molecule (FIG. 2C).

Figure 3:
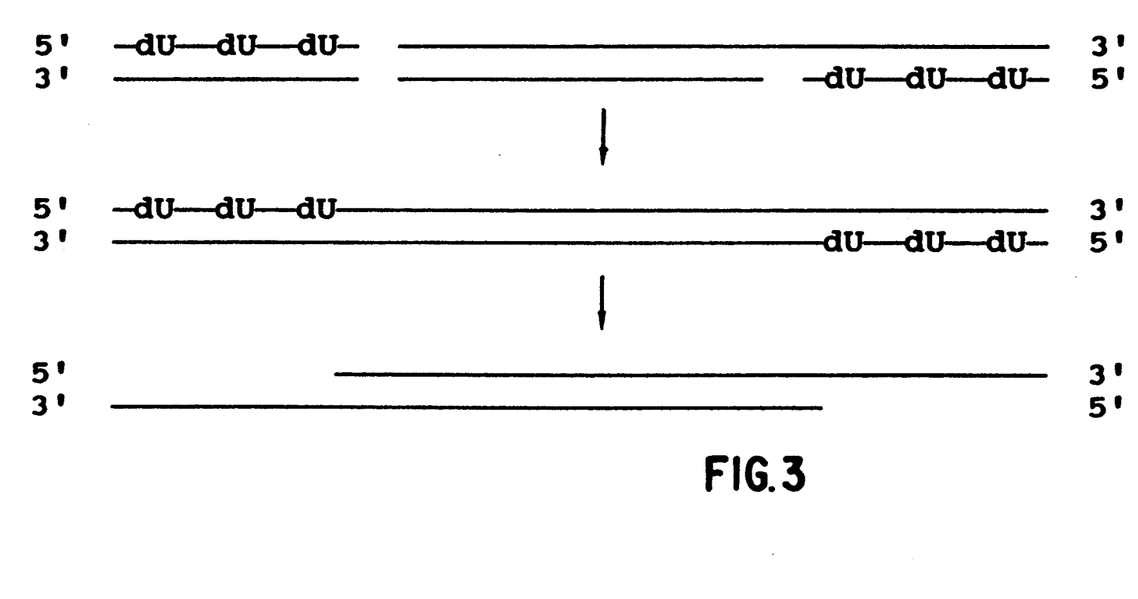
FIG. 3 shows an embodiment wherein the exo-nucleotide is incorporated into both strands of a double-stranded molecule, and used to produce a molecule having two modified termini.

As will be readily recognized, it is possible to modify both termini of the desired molecule through the ligation of the dU-containing oligonucleotide to both ends of the molecule (FIG. 3).

Figure 4A:
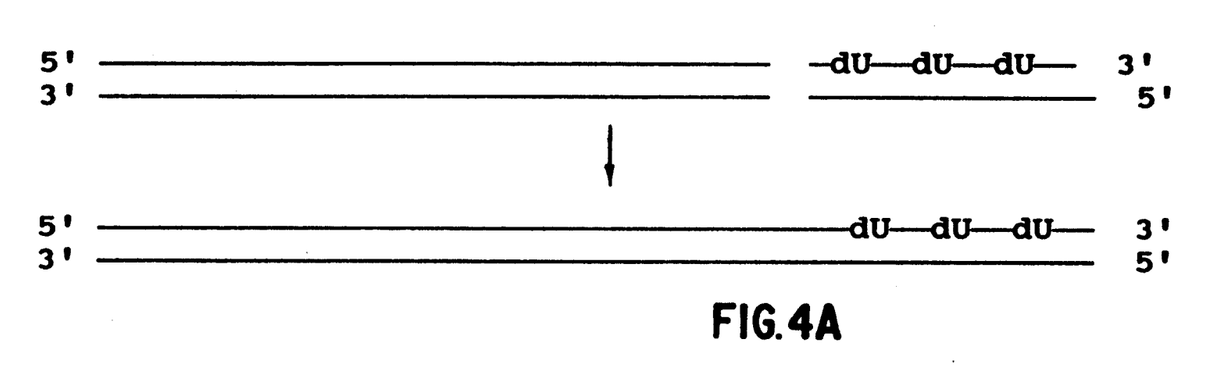
FIG. 4A describes an embodiment wherein the exo-sample nucleotide is incorporated into one strand of a double-stranded oligonucleotide to modify the 5' terminus of a molecule. The target molecule is depicted in FIG. 2A.
Figure 4B:
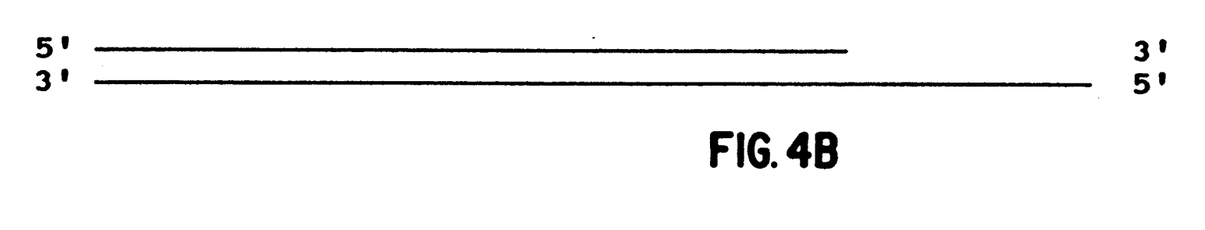
FIG. 4B illustrates the removal of the dU-containing sequence.

In order to modify the desired molecule so as to produce a protruding 5' terminus, and exo-sample nucleotide is ligated to that terminus (FIG. 4A). As in the above embodiment, treatment with UDG results in the removal of the uracil base of the dU residues, thereby producing abasic sites, which can be cleaved with Endonuclease IV, or similar enzymatic activities, to produce the desired modified molecule (FIG. 4B).

Figure 5:
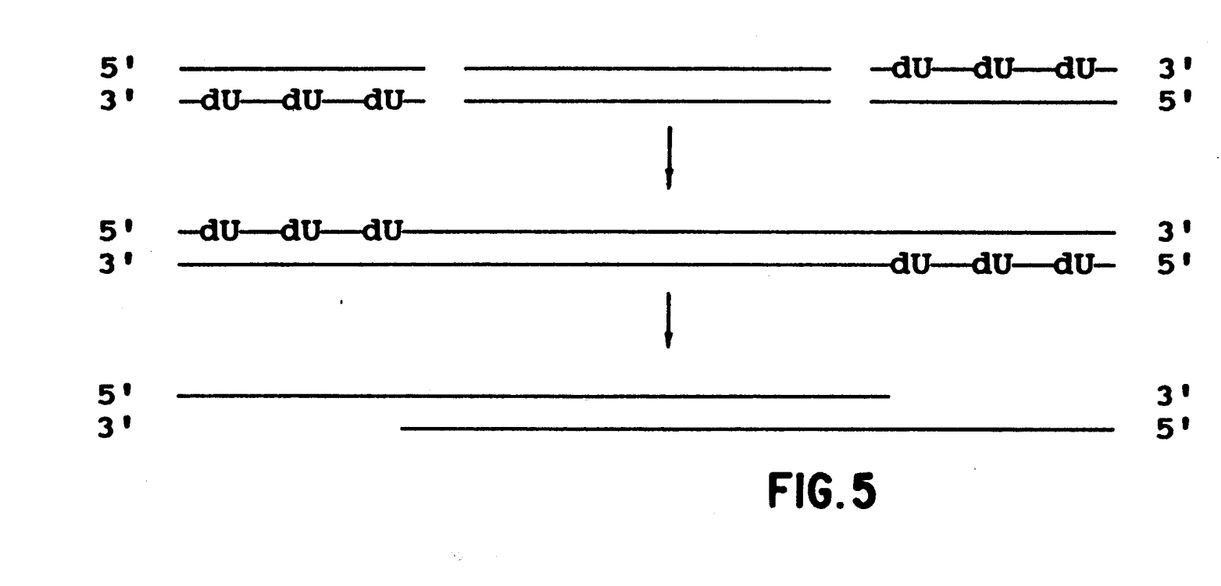
FIG. 5 shows an embodiment wherein the exo-nucleotide is incorporated into both strands of a double-stranded molecule, and used to produce a molecule having two modified termini.

Again, as in the above embodiment, it is possible to modify both termini of the desired molecule through the ligation of the dU-containing oligonucleotide to both ends of the molecule (FIG. 5).

In its most preferred embodiment, however, the present invention employs PCR to modify the 5' termini of the desired molecule.

B. MODIFICATION OF THE 5' TERMINI OF A DESIRED NUCLEIC ACID MOLECULE USING PCR AMPLIFICATION

In a second embodiment for modifying the 5' termini of a desired molecule, so as to permit the production of a molecule having overhanging 3' termini, a variation of PCR amplification may be used. In this embodiment, the desired or target sequences of the present invention are modified using PCR so as to cause them to have 5' termini which contain at least one, and preferably several exo-nucleotide molecules. For this embodiment, a specialized primer is employed. The specialized primer may be added at any stage, either initially in the PCR reaction, or after any number of cycles of amplification. When added after one or more cycles of PCR, the initial cycles of amplification are conducted using conventional primers.

C. THE SPECIALIZED PRIMERS OF THE PRESENT INVENTION

The modification of the termini of the desired molecule is preferably accomplished using PCR with two specialized primers.

Figure 6:
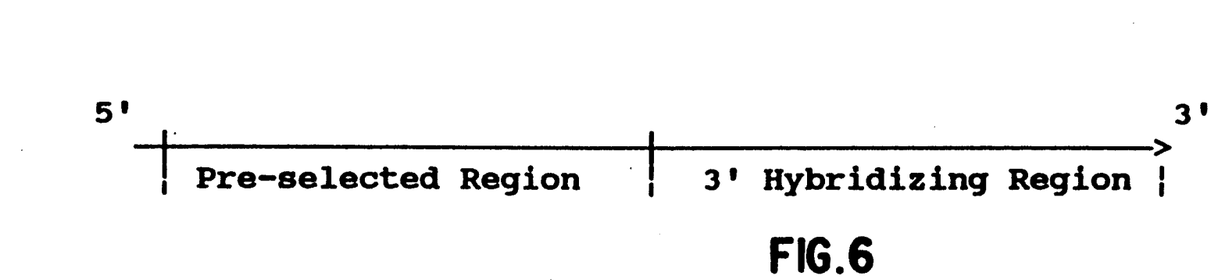
FIG. 6 shows a depiction of a primer.

Thus, each primer will be constructed such that it contains a 3' hybridizing region which is complimentary to a 5' region of one strand of a desired DNA molecule. The primers will also contain a region of predetermined and pre-selected sequence (whose length is in general of the same order of magnitude as the 3' hybridizing region of the molecule). Most preferably, the region of pre-selected sequence will be approximately 10–20, and most preferably approximately 12, bases in length. There are no constraints with regard to the nucleotide sequence of the pre-selected region of the primer molecule. The sequence can be either repetitive, palindromic, or unique. Each of the primers may thus be depicted as shown in FIG. 6.

Figure 7:
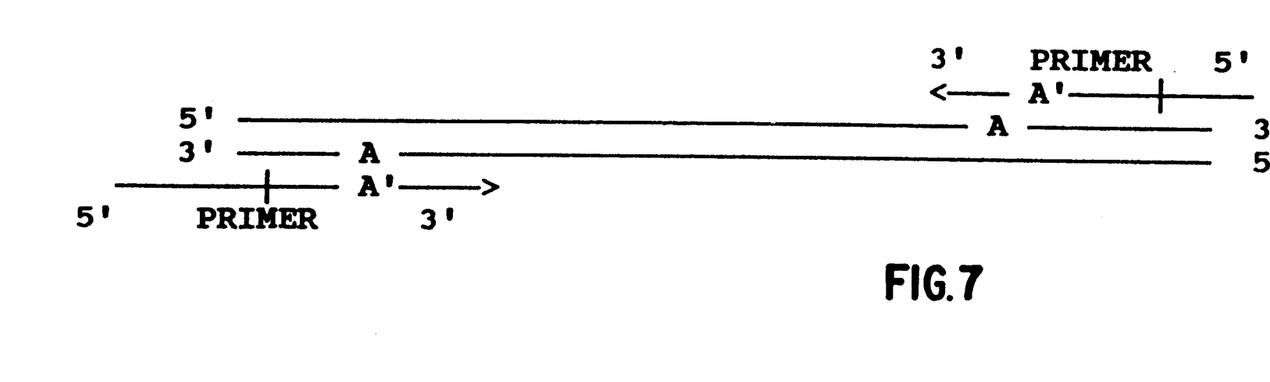
FIG. 7 shows the structure that is formed by hybridization between the primer and the target sequence by virtue of the homology between the sequences of the 3' hybridizing region and the target molecule.

As indicated, the primers will be capable of hybridizing to one strand of the target sequence by virtue of the homology between the sequences of the 3' hybridizing region and the target molecule (FIG. 7).

The 3' hybridizing region of the primer molecules need not be complementary to the precise termini of the target molecule. Indeed, the target molecule need not be a linear molecule. The purposes of the present invention will be achieved if the 3' hybridizing region of the primer molecules is capable of hybridizing to a region which either contains or flanks the sequence which is to be cloned.

Figures 8A, 8B:
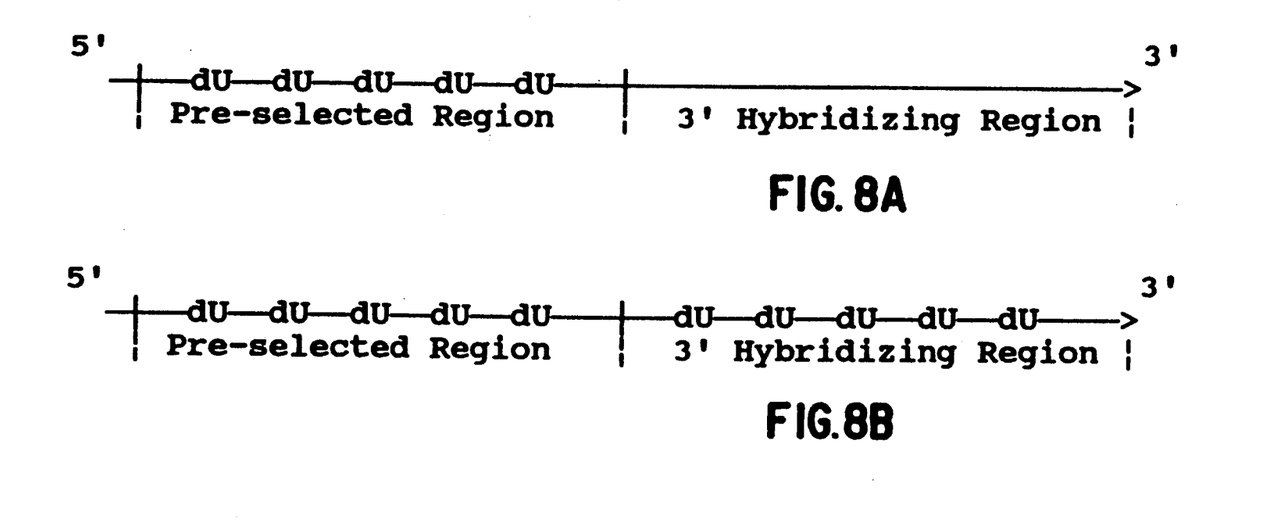
FIG. 8A shows a depiction of a dU-containing primer.
FIG. 8B shows a depiction of an embodiment wherein the entire primer contains exonucleotides.

A characteristic of the pre-selected sequence is that it will contain a number of exo-sample nucleotides, which will be preferably interspersed throughout. In a preferred embodiment, the pre-selected sequence is 12 bases long and every third base is a dU. The primer may thus be depicted as shown in FIG. 8A.

Figure 8C:
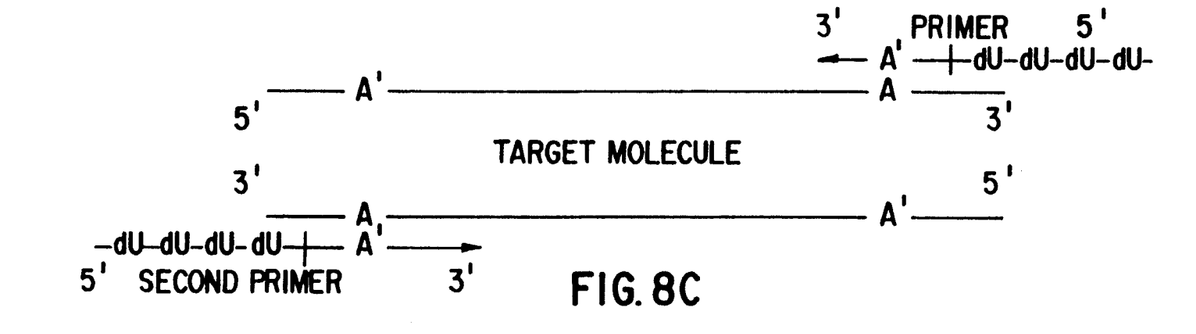
FIG. 8C shows the hybridized structure formed between the target molecules and the primers.

The 3' hybridizing region of the primer may also contain one or more exo-sample nucleotides. Indeed, in one embodiment of the invention the entire primer contains exo-sample nucleotides dispersed throughout, as shown in FIG. 8C.

Figure 9:
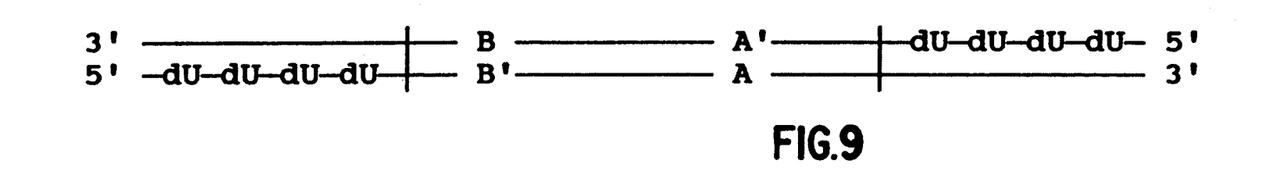
FIG. 9 shows a depiction of an-exonucleotide-containing molecule that is in a form which can readily be readily inserted into a plasmid or other vector.

The primer or primers are thus incubated in the presence of a sample which contains, or is suspected of containing the desired nucleic acid molecule. PCR, or an alternative method is then carried out in the manners described above. After at least one amplification cycle, a desired molecule can be produced by permitting the primer-extension molecules to self hybridize. As will be recognized, the resultant molecule differs from the initial desired molecule in two respects. First, it contains at both of its termini additional sequences corresponding to the pre-selected sequence region. Second, the pre-selected sequence region at the 5' end of both of the amplified strands will contain the exo-sample nucleotides of the primer molecule(s). This molecule is in a form which can be readily inserted into a plasmid or other vector in accordance with the methods of the invention. The molecule may be depicted as shown in FIG. 9.

B. THE VECTOR

Any procaryotic or eukaryotic plasmid or viral vector can be modified to permit its use in accordance with the methods of the present invention. Where the vector is a circular molecule, it is first linearized using, for example, a restriction endonuclease. The two termini of the linearized molecule are then altered to contain a sequence complimentary to one or both of the pre-selected sequences present in the amplified desired molecule. As in the case of the above-described primers, the termini of the linearized vector molecule can be altered by any of a variety of methods.

Figure 10:
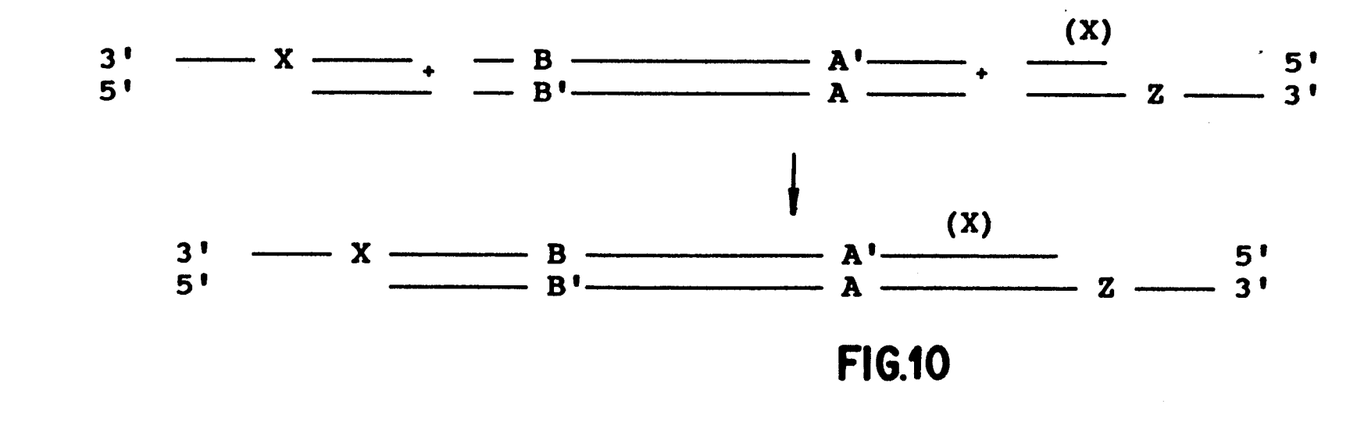
FIG. 10 shows the use of linkers to produce a linearized vector having protruding 3' termini.

In a preferred embodiment, linkers can be used and ligated to the ends of the linearized molecule to produce the desired protruding 3' termini (FIG. 10).

Figure 11:
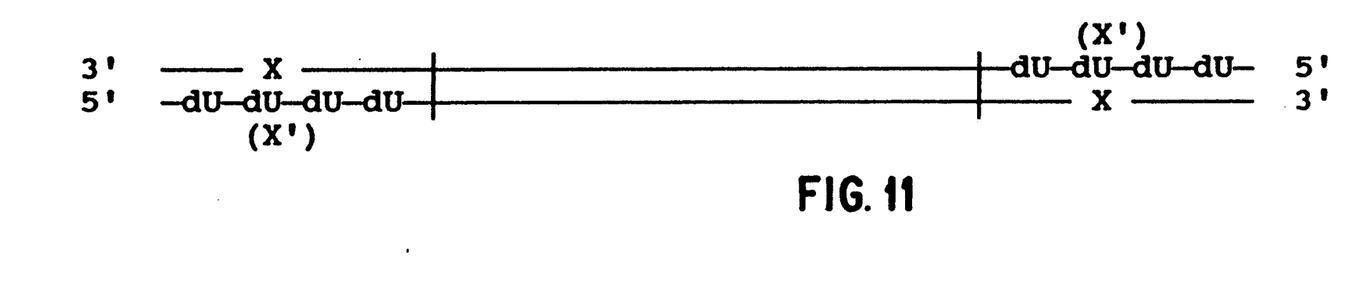
FIG. 11 shows the use of PCR and exo-sample nucleotides to produce a linearized vector having protruding 3' termini.

Alternatively, PCR can be used to produce linearized vector molecules having the suitable termini. The termini of the vector are modified to contain an exo-sample nucleotide-containing sequence which is complementary to the exo-sample nucleotide-containing sequence of the modified desired molecule. Thus, where the exo-sample nucleotide-containing sequence of the modified desired molecule has the sequence "X" the exo-sample nucleotide-containing sequence of the modified vector shall have the sequence "X'" (FIG. 11).

As will be noted, the effect of these manipulations is to produce a linearized molecule having termini which contain a pre-selected sequence which is complimentary to the pre-selected sequence contained in either or both of the termini of the modified desired sequence.

C. THE CLONING OF THE MODIFIED DESIRED SEQUENCE INTO THE MODIFIED VECTOR

Figure 12:
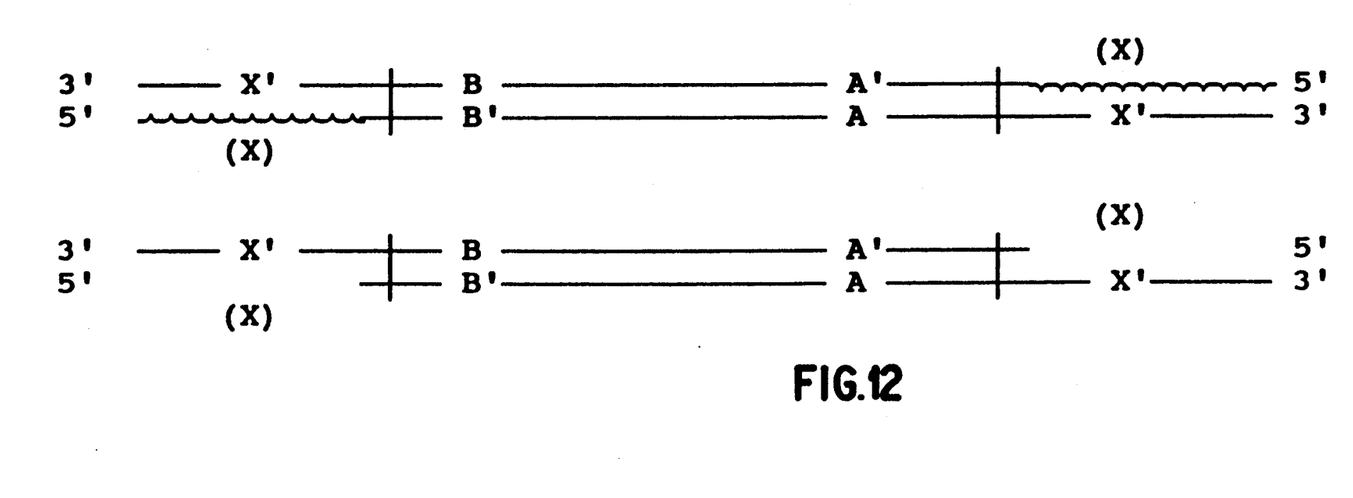
FIG. 12 shows the structures resulting from the removal of the dU residues from modified molecules.

The vector molecule and the desired molecule, as modified in the manner described above, are incubated under conditions which cause the destruction of the exo-sample nucleotide. Thus, for example, where the exo-sample nucleotide is dU, the molecules are subjected to treatment with the enzyme UDG. The resulting structures are shown in FIG. 12. As illustrated, treatment with UDG does not result in the scission of the phosphodiester backbone of the nucleic acid molecules. Rather, it results in the production of abasic sites which are thus incapable of base-pairing with complimentary sequences. The presence or absence of these abasic site-containing sequences is irrelevant to the subsequent application of the methods of the invention.

Figure 13A:
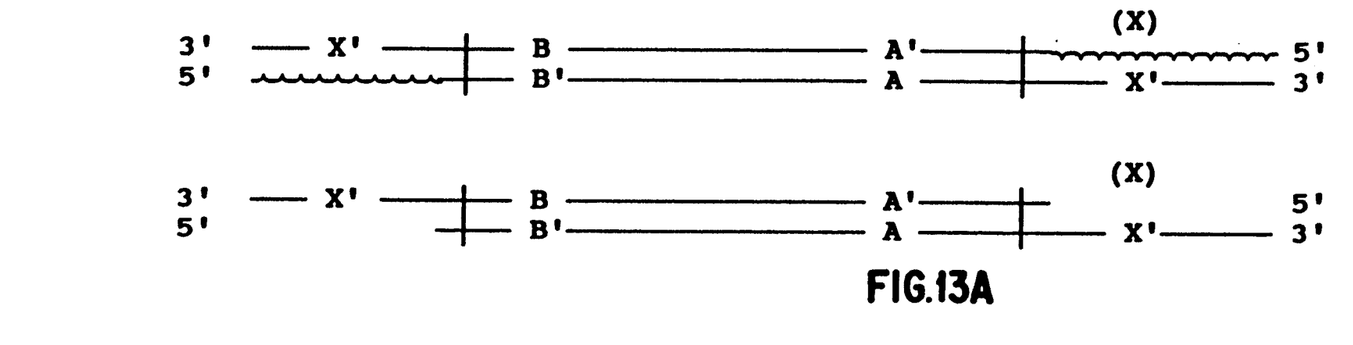
FIG. 13A shows the modified molecules after destruction of exo-sample nucleotide.
Figure 13B:
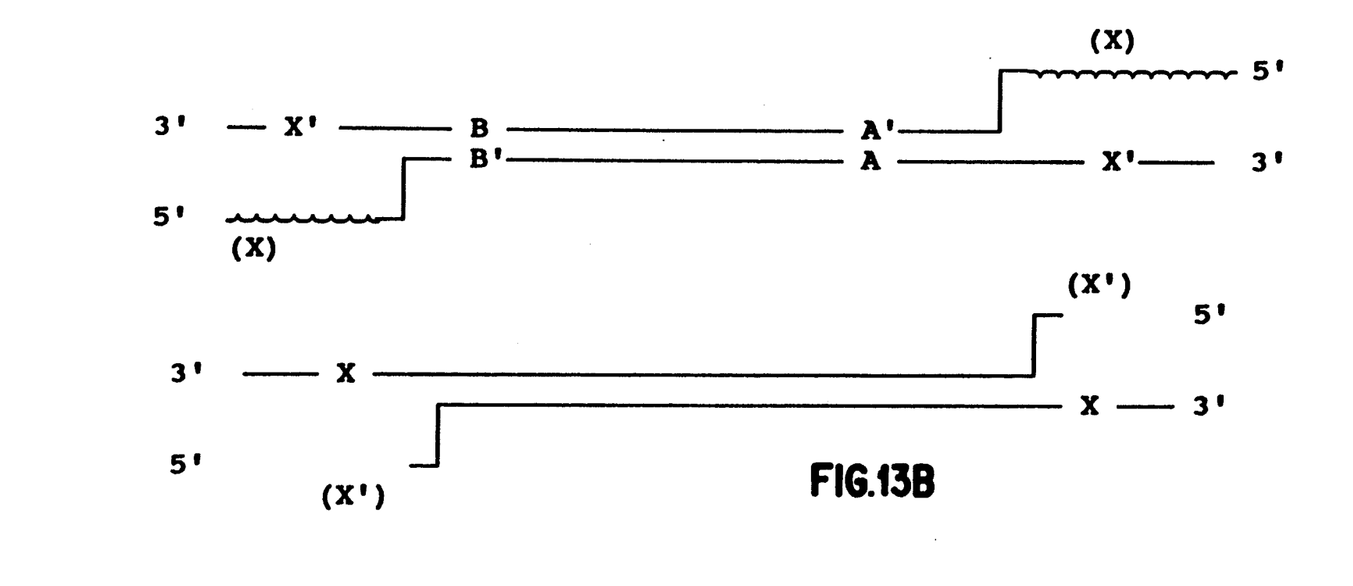
FIG. 13B illustrates the loss of base pairing capacity of the region of pre-selected sequence after the destruction of the exo-sample nucleotide.
Figure 13C:
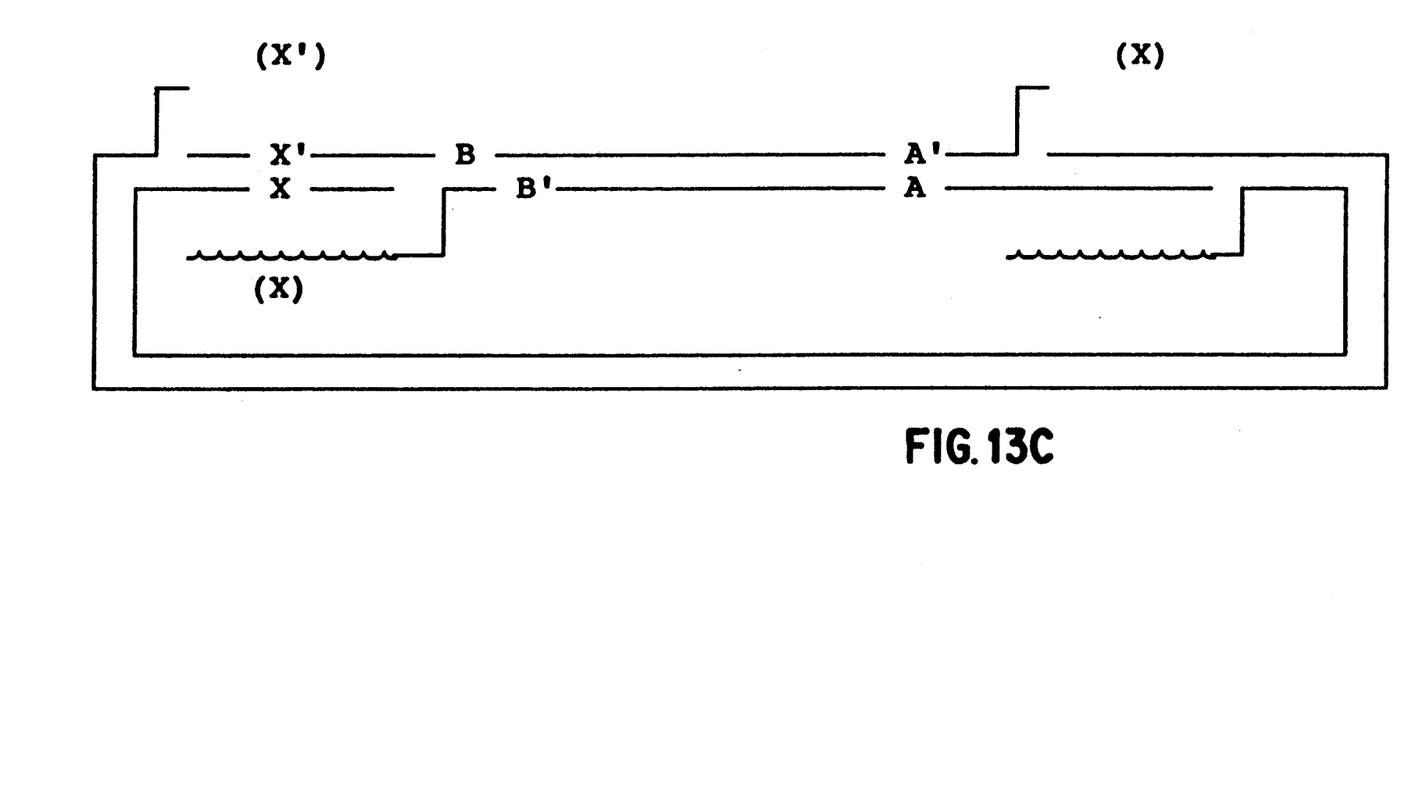
FIG. 13C illustrates the formation of the circular vector molecule containing the modified desired sequence.

Due to the complimentarity of the modified vector and desired molecule sequences, continued incubation of the modified vector with the modified desired sequences, after destruction of the exo-sample nucleotide, permits a chimeric molecule to form (FIG. 13).

As will be appreciated, the use of sequences which are complimentary to only one end of the modified desired molecule permits one to insert the sequence in a unidirectional manner. Thus, for example, if one end of the modified desired molecule had a region of pre-selected sequence X and X', and the other end of the molecule had a region of pre-selected sequence Y and Y', it would be possible to control the directionality of the insertion into the modified vector by employing a vector having regions of pre-selected sequence X' and X, and Y' and Y, respectively.

Significantly, it is not necessary to remove the abasic regions from the circular molecule prior to transformation into a suitable microbial host. Similarly, it is not necessary to treat the circular molecule with a DNA ligase or other agent in order to produce a double-stranded covalently closed circular molecule. The circular molecule described above can be used directly to transform recipient cells.

The methods of the present invention are especially amenable for use in in vitro procedures which utilize enzymes to amplify specific nucleic acid sequences and especially to PCR.

The present invention includes articles of manufacture, such as "kits." Such kits will, typically, be especially adapted to contain in close compartmentalization an instructional brochure, and a circular, or more preferably, linearized vector molecule whose 5' termini contain a region of pre-selected sequence which contains at least one exo-sample nucleotides. In a second embodiment, the kit will contain a modified vector molecule in which the exo-sample nucleotide has been destroyed to produce a protruding (i.e. overhanging) 3' terminus, or equivalently, a non-recessed 5' terminus which is incapable of base pairing with a complementary sequence.

In sub-embodiments of the above embodiments, the kit may also contain a container containing an exo-sample nucleotide-containing oligonucleotide suitable for use as a primer for modifying the termini of a desired nucleic acid molecule and/or a container which contains an enzyme capable of degrading an oligonucleotide which contains the exo-sample nucleotide. The kit may additionally contain buffers, enzymes, and the like.

Having now generally described the invention, the same will be more readily understood through reference to the following examples which are provided by way of illustration, and are not intended to be limiting of the present invention, unless specified.

EXAMPLE 1

Enzymes and reagents.

Taq DNA polymerase was purchased from Perkin Elmer-Cetus; dNTPs were from Boehringer Mannheim. Competent bacteria (DH10B), proteinase K, and restriction enzymes were from BRL. Oligonucleotides were synthesized using an ABI-380A DNA synthesizer.

Amplification of vector and human cosmid DNA.

All PCR reactions were 50 microliters covered with mineral oil using the following final buffer concentration: 50 mM KCl, 10 mM Tris-HCl (pH 8.4), 1.5 mM $MgCl_2$, and 0.2 mM of each dNTP. A Perkin Elmer-Cetus thermal cycler was used to generate Alu-PCR products as well as to analyze the inserts from subclones. After an initial 5 minutes at 93°, 35 cycles of 1 minute at 60°, 1 minute at 72° and 1 minute at 93° were used. An additional 5 minutes at 72° was used for the last cycle. Twenty to 30 ng of each of the four NotI-linearized cosmids was amplified; 1 ng of XbaI-linearized pUC119 (5) was amplified as described above. Products from PCR reactions were analyzed by 1% agarose gel electrophoresis in TAE buffer with ethidium bromide.

UDG treatment.

The vector and Alu-PCR products were precipitated with ethanol and dissolved in the following buffer (25 mM Tris-HCl [pH 7.8], 10 mM $MgCl_2$, 4 mM betamercaptoethanol, 0.4 mM ATP). Single-stranded 3' overhangs consisting of 10 nucleotides in the vector and 11 nucleotides in the Alu-PCR products were made by treating vector (225 ng) and Alu-PCR products (110 ng to 212 ng) each separately with UDG (BRL) in a final volume of 10 microliters for 10 minutes at 37°. Initial experiments used 16 units of UDG, however as little as 1 unit has been found to be sufficient. A 10 minute treatment at 65° was used following the UDG treatment.

Cloning and transformation.

UDG treated vector (45 ng) was combined with UDG treated Alu-PCR reaction products (45 ng to 106 ng) in a final volume of 20 microliters in the above Tris, $MgCl_2$, betamercaptoethanol, ATP buffer for one hour at room temperature. Five microliters from each combination were transformed in 50 microliters of DH10B competent cells (BRL) following the manufacturers recommendations, and plated onto LB plates containing ampicillin, X-gal and IPTG.

PCR analysis of transformants.

Subclones were analyzed by PCR using the Alu primer. Single white colonies were dispersed into 12 microliters of 10 mM Tris-HCl (pH 7.5), 1 mM EDTA, 50 micrograms per ml proteinase K and incubated at 55° for 15 minutes, 80° for 15 minutes, and chilled on ice. PCR components including the Alu primer were added and amplified for 30 cycles using the above protocol. Five microliters of each analysis was run on an agarose gel for sizing. Analysis of the transformants obtained using this procedure showed efficient cloning of PCR products using the exo-sample nucleotide cloning method. Control reactions where the insert DNA, or the vector DNA or the UDG treatment had been omitted resulted in no transformants, indicating that the cloning method was dependent on the procedure outlined and embodied in this application.

What is claimed is:

1. A method for incorporating a double-stranded linear desired nucleic acid molecule having a first and a second strand into a double stranded vector, comprising the steps of:
   (A) forming a modified desired nucleic acid molecule characterized in possessing a first region of pre-selected sequence at at least one terminus of a first strand, said sequence being of a length of from about 10 to about 20 nucleotides, and being composed of at least about one third exo-sample nucleotide residues selected from the group consisting of deoxyuridine, bromodeoxyuridine, and a ribonucleotide;
   (B) treating said first region of pre-selected sequence under conditions sufficient to result in the removal of at least one of said exo-sample nucleotide residues, to thereby form a protruding terminus capable of hydrogen bonding to a complementary sequence on at least one strand of said modified desired molecule;
   (C) incubating said treated modified molecule of step (B) in the presence of a modified vector having at least one protruding single-stranded terminus, and being capable of hydrogen bonding to at least one of said protruding terminus of said modified desired DNA molecule, to thereby incorporate said double-stranded linear desired nucleic acid molecule into said double stranded vector.

2. The method of claim 1 wherein only one terminus of said modified desired molecule contains said exo-sample nucleotide-containing sequence.

3. The method of claim 2 wherein said terminus is a 3' terminus of said modified desired molecule.

4. The method of claim 2 wherein said terminus is a 5' terminus of said modified desired molecule.

5. The method of claim 1 wherein said desired nucleic acid molecule is characterized in possessing a first region of pre-selected sequence at two termini, and wherein said two termini of said modified desired molecule contain said exo-sample nucleotide-containing sequence.

6. The method of claim 5 wherein both of said termini are 3' termini of said modified desired molecule.

7. The method of claim 5 wherein both of said termini are 5' termini of said modified desired molecule.

8. The method of claim 1 wherein said termini of said first and second strands of said desired DNA molecule contain a plurality of said exo-sample nucleotide residues.

9. The method of claim 1 wherein in step (B), said exo-sample nucleotide residues are treated under conditions sufficient to remove at least one of said residues, to thereby form an abasic site.

10. The method of claim 9 wherein step (B) additionally comprises treating said abasic site with Endonuclease IV under conditions sufficient to cleave the modified desired molecule at said abasic site.

11. The method of claim 1 wherein said regions of pre-selected sequence of said modified desired DNA molecule are identical.

12. The method of claim 1 wherein in step (C), said modified vector has two protruding single strand termini, wherein said termini are produced through the action of a restriction endonuclease.

13. The method of claim 1 wherein in step (C), said modified vector has two protruding single strand termini, wherein said termini are produced through the ligation of an oligonucleotide to said vector.

14. The method of claim 1 wherein in step (C), said modified vector has two protruding single strand termini, wherein said termini are produced by
(I) adding to said vector:
(i) a first region of pre-selected sequence at a 5' terminus of a first strand, said sequence containing at least one exo-sample nucleotide residue selected from the group consisting of deoxyuridine, bromodeoxyuridine, and a ribonucleotide;
(ii) a second region of pre-selected sequence at a 5' terminus of a second strand, said sequence containing at least one exo-sample nucleotide residue selected from the group consisting of deoxyuridine, bromodeoxyuridine, and a ribonucleotide; and
(II) treating said first and second regions of pre-selected sequence under conditions sufficient to result in the removal of at least one of said exo-sample nucleotide residues, to thereby form said modified vector having said protruding 3' termini.

* * * * *